United States Patent [19]

Amrein et al.

[11] Patent Number: 5,221,672
[45] Date of Patent: Jun. 22, 1993

[54] PHARMACEUTICAL COMPOSITIONS CONTAINING BRETAZENIL AND METHODS OF USING THEM

[75] Inventors: Roman Amrein, Bettingen, Switzerland; Jean-Paul Laurent, Mulhouse, France

[73] Assignee: Hoffmann-La Roche Inc., Nutley, N.J.

[21] Appl. No.: 800,791

[22] Filed: Nov. 27, 1991

[30] Foreign Application Priority Data

Nov. 29, 1990 [CH] Switzerland ............ 3776/90

[51] Int. Cl.$^5$ ............................................ A61K 31/55
[52] U.S. Cl. .................................... 514/219; 514/923
[58] Field of Search ............... 514/214, 215, 219, 923

[56] References Cited

U.S. PATENT DOCUMENTS

| 4,352,815 | 10/1982 | Hunkeler et al. | 514/219 |
| 4,353,827 | 10/1982 | Hunkeler et al. | 540/494 |
| 4,861,772 | 8/1989 | Merz | 514/219 |
| 4,914,095 | 4/1990 | Merz | 514/219 |

FOREIGN PATENT DOCUMENTS

WO90/02737 3/1990 Int'l Pat. Institute .

OTHER PUBLICATIONS

Saletu, et al., *Int. J. Clin. Pharmacol. Ther. and Toxicol.*, vol. 27, No. 2 (1989).

Belzung, et al., *Psychopharmacolog*, vol. 97, 338–391 (1989).

Schreur, et al., *Society for Neuroscience Abstracts*, vol. 15, No. 2, (1989).

Pieri, et al., *Drugs of the Future*, vol. 13, No. 8 730–735 (1988).

Berkow, et al., *The Merck Manual*, 1376–1377 (1987).

*Primary Examiner*—Frederick E. Waddell
*Assistant Examiner*—K. Waddington
*Attorney, Agent, or Firm*—George M. Gould; George W. Johnston; William Krovatin

[57] ABSTRACT

The compound t-butyl (S)-8-bromo-11,12,13,13a-tetrahydro-9-oxo-9H-imidazo[1,5-a]pyrrolo[2,1-c][1,4]benzodiazepine-1-carboxylate of the formula

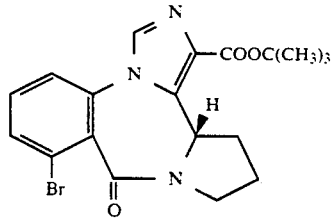

can be used for the preparation of medicaments for the treatment of sleep disorders and also as a medicament for the treatment of sleep disorders.

3 Claims, No Drawings

PHARMACEUTICAL COMPOSITIONS CONTAINING BRETAZENIL AND METHODS OF USING THEM

BRIEF SUMMARY OF THE INVENTION

The invention relates to the use of bretazenil, also known as t-butyl (S)-8-bromo-11,12,13,13a-tetrahydro-9-oxo-9H-imidazo-[1,5-a]pyrrolo[2,1-c][1,4]benzodiazepine-1-carboxylate, of the formula

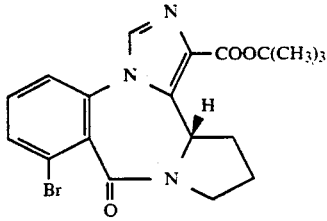

to induce sleep corresponding largely to natural sleep in the treatment of sleep disorders. In another aspect, the invention relates to the use of bretazenil for the preparation of medicaments for the treatment of sleep disorders and a method and medicament for the treatment of sleep disorders are further objects of the present invention.

BACKGROUND OF THE INVENTION

Bretazenil is a known substance. Its preparation is described, for example, in European Patent Publication No. 59 391 which is incorporated herein by reference. The anticonvulsive and anxiolytic properties of this compound are also described in this publication.

Bretazenil has a high affinity to the benzodiazepine receptor (BZR), the modulatory part of the receptor for the amino acid GABA. GABA is an inhibiting messenger (neurotransmitter) of certain nerve cells (neurons) of the brain. The release of GABA by one type of neuron causes inhibition of the excitability of other neurons, which can manifest itself, for example, in anxiolytic, anticonvulsive, muscle relaxant or sedative-hypnotic activity. Three main types of substances have been found which bind to the BZR and which are denoted as ligands: (1) The agonists, which intensify the inhibition by GABA; (2) the so-called inverse agonists which reduce the activity of GABA; and (3) the antagonists which do not influence the activity of GABA, but which prevent its intensification or reduction by agonists or inverse agonists at the BZR (see Haefely, W., Handbook of Anxiety 3: 165-188, 1990). Substances from the three groups of ligands which are active on the BZR generally have a high affinity to this receptor, but differ by the so-called relative intrinsic effectiveness, i.e. the capability of influencing the activity of GABA. While pure antagonists occupy the BZR, but do not influence the activity of GABA, full agonists or inverse agonists produce maximum intensification or reduction of the inhibiting activity of GABA at the BZR. It is conceivable that between the extremes there are substances with different degrees of intrinsic effectiveness and that such substances would also be found. These substances behave as weak agonists or inverse agonists, but significantly weaker than the activity of the actual full agonists. Such substances are therefore partial agonists or partial inverse agonists.

It has now been found that bretazenil is one such partial agonist or partial agonist at the BZR. In animal experiments it has been established that bretazenil has a high affinity to the BZR, but bretazenil only achieves effects which correspond to those of lower dosages of benzodiazepines (BZD), for example, diazepam. The characteristic effects and side-effects of increasing dosages of a BZD such as sedation, muscle relaxation, ataxia and amnesia could not be shown or could be shown only in subtoxic dosages for bretazenil in classical animal experiments.

It has now surprisingly been found that bretazenil can induce sleep in healthy, male and female volunteers even in low dosages and that the induced sleep corresponds largely to natural sleep.

DETAILED DESCRIPTION OF THE INVENTION

The invention relates to the use of bretazenil, also known as t-butyl (S)-8-bromo-11,12,13a-tetrahydro-9-oxo-9H-imidazo-[1,5a]pyrrolo[2,1-c][1,4]benzodiazepine-1-carboxylate, of the formula

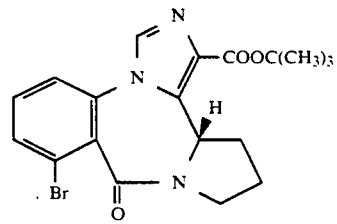

to induce sleep corresponding largely to natural sleep in the treatment of sleep disorders, e.g. hypersomnias, relative insomnias, circadian dysfunction, parasomnias, REM sleep behavior disorder, sleep walking and sleep terrors.

The sleep inducing property of bretazenil can be determined on the basis of the double blind study described hereinafter:

Six male volunteers and six female volunteers with an average age of 24 years and an average weight of 58 kg took part in the study. The volunteers were required to take 0.5, 1 or 2 mg of bretazenil in tablet form after 21 hours. This took place after the volunteers had taken identical placebo tablets on two previous evenings. The second placebo night served as the reference (pre-control). Placebo was again administered on the evening of the day after bretazenil (post-control). The volunteers spent the four nights of one session in a sleep laboratory. Their brain current curves (EEG) and body movements were recorded on magnetic tape and thereafter evaluated using a computer. This method permits the exact recording of the sleep profile.

The results determined in this study (see Table I) show quite clearly that bretazenil was effective in all tested dosages. Bretazenil shortened drastically the time needed to fall asleep (sleep latency) and lengthened the total sleep per night by lengthening the normal sleep (non REM sleep), and reducing the number of intermittent short waking phases. Likewise, bretazenil reduced the number of body movements during sleep. Thus, bretazenil brought about a more rapid falling asleep and a lengthening and stabilization of the sleep. During normal sleep bretazenil either did not reduce the deep sleep stages 3 and 4 or reduced these stages only insignificantly, but overall it did lengthen the duration of the middle sleep stage 2. Middle sleep stage 2 is characterized by the appearance of so-called sleep spikes in the EEG pattern. The number of sleep spikes was, however, unaltered. However, the number of K complexes, another characteristic pattern in the EEG, was reduced in stage 2. These K complexes can be traced back to disturbing acoustic signals which reach the sleeping brain. The reduction of K complexes therefore, points to a deepening of the sleep. The superficial sleep of stage 1 was shortened by bretazenil.

The sleep of a healthy human being is usually structured in five sleep cycles with each cycle being terminated with a dream phase. Bretazenil does not alter the number of cycles, but lengthens both the first cycle and the period until the first dream phase occurs (REM sleep latency). The dream sleep, also referred to as REM sleep because rapid eye movements occur therein, was, however, only immaterially shortened overall by bretazenil. The closeness of the rapid eye movements (REMs) in the REM sleep was decreased.

TABLE I

Effects of bretazenil on the sleep of healthy volunteers

| | Dosage administered in mg p.o. | | |
|---|---|---|---|
| | 0.5 | 1 | 2 |
| Sleep latency | 33* | 30* | 20* |
| Total sleep | +45 min* | +44 min* | +45 min* |
| Intermittent waking phases | 32* | 25* | 22* |
| Movements | 80* | 74* | 69* |
| Non REM sleep | +60 min* | +60 min* | +62 min* |
| Stage 1 | 98 | 65* | 79 |
| Stage 2 | 130* | 128* | 136* |
| Stage 3 | 90 | 90 | 87 |
| Stage 4 | 87* | 103 | 79* |
| Spikes in stage 2 | 101 | 107 | 107 |
| K complexes in stage 2 | 71* | 63* | 61* |
| Duration of first sleep cycle | 154* | 189* | 198* |
| REM sleep latency | 165* | 206* | 217* |
| REM sleep duration | 91 | 83 | 85 |
| REMs in REM sleep | 84 | 49* | 31* |

All values, except total sleep and non REM sleep, are in % and relate to the pre-control. The absolute increase in minutes is given for total sleep and non REM sleep.

*$p<0.05$

In the practice of the invention, bretazenil can be used in the form of pharmaceutical preparations for peroral, rectal and parenteral administration. Tablets, coated tablets, dragees, hard and soft gelatine capsules, suppositories, solutions, emulsions or suspensions are examples of such preparations. Perorally administrable forms, especially tablets, are preferred dosage forms.

Bretazenil is processed with pharmaceutically inert, inorganic or organic carrier materials in order to manufacture pharmaceutical preparations. Although not intended to be an exhaustive list, examples of suitable carrier materials for tablets, coated tablets, dragees and hard gelatine capsules are, for example, lactose, maize starch or derivatives thereof, talc, stearic acid or its salts and the like. Vegetable oils, waxes, fats, semi-solid and liquid polyols and the like are, for example, suitable for soft gelatine capsules. Natural or hardened oils, waxes, fats, semi-solid and liquid polyols and the like are, for example, suitable for suppositories. Suitable carrier materials for the manufacture of solutions, emulsions and suspensions are, for example, water, polyols, saccharose, invert sugar, glucose and the like.

Moreover, the pharmaceutical preparations can contain the usual preservatives, solubilizers, stabilizers, wetting agents, emulsifiers, sweeteners, colorants, flavorants, salts for varying the osmotic pressure, buffers, coating agents and/or antioxidants.

As already mentioned, bretazenil can be used in the treatment of sleep disorders. The dosages can vary according to the severity of the sleep disorders and the age and weight of the patient and will, of course, be fitted to the individual requirements in each particular case. In general, in the case of peroral administration a dosage of about 0.25 to about 5 mg should be appropriate.

The following Example describes a dosage form which is suitable for the practical application of the present invention. It is, however, in no way intended to limit the scope of the present invention.

| Example (tablet) | |
|---|---|
| Bretazenil | 0.5 mg |
| Lactose | 126.5 mg |
| Maize starch | 54.0 mg |
| Polyvinylpyrrolidone | 8.0 mg |
| Sodium carboxymethylstarch | 10.0 mg |
| Magnesium stearate | 1.0 mg |
| Tablet weight | 200.0 mg |

Bretazenil, the lactose and the maize starch are mixed and granulated with an aqueous solution of polyvinylpyrrolidone. The dried and pulverized granulate is mixed with the sodium carboxymethylstarch and the magnesium stearate, whereupon the mixture is pressed to tablets having a weight of 200 mg.

We claim:

1. A method of inducing sleep corresponding largely to natural sleep which comprises administering to a host requiring such treatment an effective amount of bretazenil, t-butyl (S)-8-bromo-11,12,13, 13a-tetrahydro-9-oxo-9H-imidazo[1,5-a]pyrrolo[2,1-c][1,4]benzodiazepine-1-carboxylate.

2. A method according to claim 1 wherein the effective amount is from about 0.25 mg to about 5 mg of bretazenil.

3. A method according to claim 1 wherein the effective amount is from about 0.5 mg to about 2 mg of bretazenil.

* * * * *